United States Patent [19]

Chiang et al.

[11] Patent Number: 5,358,858
[45] Date of Patent: Oct. 25, 1994

[54] PROCESS FOR PREPARING PHYCOERYTHRIN FROM BANGIA ATROPURPUREA AND PORPHYRA ANGUSTA

[75] Inventors: Young-Meng Chiang; Hong-Nong Chou, both of Taipei, Taiwan

[73] Assignee: National Science Council, Taipei, Taiwan

[21] Appl. No.: 214,374

[22] Filed: Mar. 17, 1994

[51] Int. Cl.$^5$ .......................... C12P 21/00; C12N 1/12
[52] U.S. Cl. ...................... 435/71.1; 435/41; 435/257.1; 435/946; 435/968; 436/501; 436/800
[58] Field of Search .............. 435/71.1, 41, 257.1, 435/946, 968; 436/800, 501

[56] References Cited

U.S. PATENT DOCUMENTS

| | | | |
|---|---|---|---|
| 4,078,332 | 3/1978 | Savins | 435/257.1 |
| 4,079,544 | 3/1978 | Savins | 435/257.1 |
| 4,235,043 | 11/1980 | Harpsawa et al. | 47/1.4 |
| 4,752,638 | 6/1988 | Nowinski et al. | 530/405 |
| 4,857,474 | 8/1989 | Waterbury et al. | 530/370 |
| 5,055,402 | 10/1991 | Greene et al. | 435/946 |

OTHER PUBLICATIONS

JPOABS 63-263095 Abstract "Production of Phycoeryhrin" Tanaka Published Abs. Feb. 17, 1989 Japan Patent 63263095 (Oct. 31, 1988).

JPOABS 62-100294 Abstract "Method of Extracting Red Alga Belonging to Genus Porphyra" Hara et al. Published Res. Oct. 14, 1987, Japan Patent 62100294 (May 9, 1987).

*Primary Examiner*—Herbert J. Lilling
*Attorney, Agent, or Firm*—Fish & Richardson

[57] ABSTRACT

A process for preparing phycoerythrin from *Bangia atropurpurea* or *Porphyra angusta* is disclosed. Spores of *Bangia atropurpurea* or *Porphyra angusta*, derived from their thalli, are cultivated under a controlled condition to germinate filaments. Phycoerythrin is then resulted from the extraction of filaments which are processed through drying powder-mill grinding, water or phosphate percolating and ammonium sulfate salting-out. The phycoerythrin is further purified by gel filtration. This process yields the phycoerythrin of 99% purity.

9 Claims, No Drawings

PROCESS FOR PREPARING PHYCOERYTHRIN FROM BANGIA ATROPURPUREA AND PORPHYRA ANGUSTA

BACKGROUND OF THE INVENTION

The present invention relates to a process for preparing phycoerythrin from *Bangia atropurpurea* or *Porphyra angusta* filaments.

Natural pigment proteins from plants are safe when used in food and drink. The pigments are stable in mild heat, and acidic or basic solutions. Therefore they can be utilized in food and cosmetics as coloring agent. In additional, the pure form of the pigment can be used in fluorescent labeling of antibodies that were applied as diagnostic agent in immunological, clinical, cell biological and biochemical research.

Phycocyanin and phycoerythrin are two currently used natural pigment proteins, and have been applied in many fields. As the major raw material for phycocyanin is easy-growing blue-green algae such as Spirulina and Microcystis and a large number of methods of algae cultivation and phycocyanin preparation therefrom have been developed, the supply of phycocyanin does not cause a problem. However, the quantity of phycoerythrin is still few and the price is high due to the shortage of raw material available and the difficulty in processing for the commercial production of phycoerythrin.

Most of the phycoerythrin is extracted from red algae thalli such as Porphyra and Ceramium, and only a little amount of phycoerythrin are extracted from Porphyridium, which is now available from tank cultivation.

Although increasing amount of wild red algae and cultivated Porphyra are utilized as raw material for phycoerythrin, most of them contain a high gel content, making the extraction of phycoerythrin from them be very difficult, especially for dried algae. Furthermore, the quantity and quality of wild algae are apt to be influenced by the seasons and the ambient temperature. These elements make the production of phycoerythrin from wild and cultivated Porphyra even more difficult.

Extracting phycoerythrin from Porphyridium also has its difficulties, because the collection of single-cell is usually labor-intensive as well as time-consuming and the soluble polysaccharide secreted during the cultivation of algae will deter the cell collection and influence the extraction of phycoerythrin.

SUMMARY OF THE INVENTION

It is therefore an object of this invention to provide an economical, rapid and efficient process for preparing phycoerythrin.

It has been found that in the alternation of generations of *Bangia atropurpurea* and *Porphyra angusta*, filamentous plants thereof do not contain gel and can thus be maintained under some controlled conditions. The invention takes advantage of these findings to provide a process for preparing phycoerythrin from filamentous phase of *Bangia atropurpurea* and *Porphyra angusta*.

Specifically, the process of the invention includes the following steps: a) providing a mature thalli of *Bangia atropurpurea* and *Porphyra angusta*; b) cultivating the thalli in a cultured medium (SWM-III medium) to obtain spores; c) cultivating the spores in a condition wherein the temperature, light intensity and photoperiod are respectively 15° C.–25° C., 1000 1x–4000 1x and 10:14–16:8 (light:dark) to obtain filaments; d) cutting the filaments into segments and cultivating them in a larger container in the above condition until the cultivated filaments grow to the required amount; e) collecting the cultivated filaments, drying and grinding them into powder; f) adding the powder to a liquid selected from the group consisting of water and phosphate solution, and stirring to obtain a solution containing the phycoerythrin; and g) salting out the phycoerythrin from the solution.

DETAILED DESCRIPTION OF THE INVENTION

The invention will be described in more detail with reference to the preferred embodiments of the invention.

According to the process of the invention, mature *Bangia atropurpurea* or *Porphyra angusta* thalli are collected from sea and washed with sterilized seawater. After a short time of air-drying, they are placed into culture medium (SWM-III medium). After a few hours, spores will be released from the *Bangia atropurpurea* or *Porphyra angusta* thalli. The released spores are then removed from original medium and placed in a growth chamber wherein the temperature, illuminance and light/dark ratio is 25° C., 500 1x-1000 1x and 10:14–16:8. After the spores germinate to branched filaments, the filaments are transferred to SWM-III medium-containing flasks, and cultivated in the above condition until they form colonies. The filamentous colonies are then cut into small segments using sterilized grinder and moved to a larger space, such as a tank, in order to facilitate the further growth. After they are transferred into a larger space, more filaments are generated. The filamentous colonies are cut again for further growth until the required amount is acquired. Note that when the filamentous colonies are cultivated in a large tank, fresh air (300 ml air/min) must be supplied to the tank. The filaments are then collected and filtered by a net of 100–400 mesh. The culture medium can be recovered and reused.

The collected and filtered *Bangia atropurpurea* or *Porphyra angusta* filaments are then fast dried in vacuum or by warm air and ground into powder. The powder is added to a solution of phosphate or water and mixed completely. Debris are removed by centrifugation to obtain a clear-red pigment solution. Crude phycoerythrin can then be obtained by adding $(NH_4)_2SO_4$ to make it as 20%–30% saturated solution to remove unnecessary proteins, followed by sedimentation with 60%–65% $(NH_4)_2SO_4$ saturated solution. The crude phycoerythrin obtained has an $OD_{565}/OD_{280}$ of 1.4–1.6 and become food-grade and cosmetics-usable pigments.

The crude precipitated phycoerythrin can be further purified by gel filtration chromatography. For example, after purifying with Sephadex G200 chromatography once, the $OD_{565}/OD_{280}$ ratio of the produced phycoerythrin can reach to 3.3–3.7. After repeated purification process, the $OD_{565}/OD_{280}$ ratio of phycoerythrin can reach to 5.1–5.2. The purity of the phycoerythrin is about 99% when tested with SDS electrophoresis. This indicates that the phycoerythrin produced by the process of the invention can be used as reagents for immunoassay.

EXAMPLE 1

Mature *Bangia atropurpurea* thalli were collected from sea and washed with sterilized seawater by using a brush. The washed thalli after a short-time air-drying were then placed into a petri dish containing SWM-III medium and several cover glasses on its bottom. After spores were released from the *Bangia atropurpurea* thalli and fall down to the cover glasses the cover glasses carrying the released spores were then transferred to a new petri dish containing the same medium in a growth chamber wherein the temperature, illuminance and light/dark ratio was 20° C., 2000 1x and 12:12. After a few days, they germinated to form branched filaments. The branched filaments were then removed from the cover glasses and placed into flasks containing SWM-III medium, and cultivated in the above condition until filamentous colonies are formed. The colonies were then cut in a sterilized blender into small segments and transferred into a larger tank for further growth. In the larger tank, fresh air (300 ml air/min) was supplied. The *Bangia atropurpurea* filaments were collected and filtered with a net of 200 mesh after 40 days. The weight of the dried *Bangia atropurpurea* is 31.4 times the weight of the inoculated filaments.

EXAMPLE 2

The procedures as described in example 1 were repeated, except that the condition of Bangia atropurpurea growth was changed to: temperature: 20° C., illuminance: 2000 1x and light/dark ratio: 14:10. After cultivating for 40 days, the weight of the dried *Bangia atropurpurea* is 30.8 times the weight of the inoculated filaments.

EXAMPLE 3

The procedures as described in example 1 were repeated, except that the condition of *Bangia atropurpurea* growth was changed to: temperature: 20° C., illuminance: 4000 1x and light/dark ratio: 12:12. After cultivating for 40 days, the weight of dried *Bangia atropurpurea* is 30.5 times the weight of the inoculated filaments.

EXAMPLE 4

The procedures as described in example 1 were repeated, except that the condition of *Bangia atropurpurea* growth was changed to: temperature: 20° C., illuminance: 4000 1x and light/dark ratio: 14:10. After cultivating for 40 days, the weight of dried *Bangia atropurpurea* increased 30.1 times the weight of the inoculated filaments.

EXAMPLE 5

The procedures as described in example 1 were repeated, except that the condition of *Bangia atropurpurea* growth was changed to: temperature: 15° C., illuminance: 2000 1x and light/dark ratio: 12:12. After cultivating for 40 days, the weight of dried *Bangia atropurpurea* is 21.6 times the weight of the inoculated filaments.

EXAMPLE 6

The procedures as described in example 1 were repeated, except that the condition of *Bangia atropurpurea* growth was changed to: temperature: 25° C., illuminance: 2000 1x and light/dark ratio: 12:12. After cultivating for 40 days, the weight of dried *Bangia atropurpurea* is 18.1 times the weight of the inoculated filaments.

EXAMPLE 7

The procedures as described in example 1 were repeated, except that the condition of *Bangia atropurpurea* growth was changed to: temperature: 25° C., illuminance: 4000 1x and light/dark ratio: 14:10. After cultivating for 40 days, the weight of dried *Bangia atropurpurea* is 15.6 times the weight of the inoculated filaments.

EXAMPLE 8

The procedures as described in example 1 were repeated, except that the condition of Bangia atropurpurea growth was changed to: temperature: 30° C., illuminance: 1000 1x and light/dark ratio: 10:14. After cultivating for 40 days, the weight of dried *Bangia atropurpurea* is 19.3 times the weight of the inoculated filaments.

EXAMPLE 9

The procedures as described in example 1 were repeated, except that the condition of *Bangia atropurpurea* growth was changed to: temperature: 30° C., illuminance: 1000 1x and light/dark ratio: 16:8. After cultivating for 40 days, the weight of dried *Bangia atropurpurea* is 14.3 times the weight of the inoculated filaments.

EXAMPLE 10

5 g of *Bangia atropurpurea* filaments were collected and fast dried by warm air, and then ground to 2.4 grams of powder by an autogrinding machine. The powder and a 70 ml solution of 10 mM potassium phosphate were thoroughly mixed. The mixture was then separated by centrifugation at 6000 rpm for 10 min at 4° C. This resulted in a clear-red pigment solution. Seventeen grams solid $(NH_4)_2SO_4$ was added to the solution to form a 20% saturated solution of $(NH_4)_2SO_4$ and unwanted proteins precipitated therefrom. The solution was then centrifuged at 6000 rpm for 10 min at 4° C., to remove the unwanted proteins to obtain a purer pigment protein solution thereafter. 113 g of solid $(NH_4)_2SO_4$ was added to the pigment solution to form a 65% $(NH_4)_2SO_4$ solution that was then centrifuged under the same conditions to obtain the phycoerythrin precipitate. The precipitated phycoerythrin was then dialyzed with 10 mM potassium phosphate, which resulted in the formation of the crude phycoerythrin solution having $OD_{565}/OD_{280}$ of 1.5.

The crude phycoerythrin was then purified by Sephadex G200 gel filtration chromatography using a column of 120 cm height. Total of 100 tubes of eluate, each tube contains 6 ml, was collected. It was found that the eluates in the tubes from #35 to #37 contained phycoerythrin due to their high 565 nm absorption. The phycoerythrin solution thus obtained has an OD ratio of 3.5. Repeated purification yielded a final phycoerythrin solution having an OD ratio of 5.1. The purity of the phycoerythrin is 99% when analyzed with SDS electrophoresis, indicating the phycoerythrin can be used in immunoassay.

EXAMPLE 11

The procedures as described in example 1 were repeated, except that *Porphyra angusta* instead of *Bangia atropurpurea* was used, and the condition of the *Porphyra angusta* growth was changed to: temperature: 20°

C., illuminance: 4000 lx and light/dark ratio: 12:12. After cultivating for 40 days, the weight of dried *Porphyra angusta* is 32.4 times the weight of the inoculated filaments.

EXAMPLE 12

The procedures as described in example 11 were repeated, except that the condition of the *Porphyra angusta* growth was changed to: temperature: 20° C., illuminance: 4000 lx and light/dark ratio: 14:10. After cultivating for 40 days, the weight of dried *Porphyra angusta* is 30.1 times the weight of the inoculated filaments.

EXAMPLE 13

The procedures as described in example 11 were repeated, except that the condition of the *Porphyra angusta* growth was changed to: temperature: 20° C., illuminance: 2000 lx and light/dark ratio: 12:12. After cultivating for 40 days, the weight of dried *Porphyra angusta* is 18.3 times the weight of the inoculated filaments.

EXAMPLE 14

The procedures as described in example 11 were repeated, except that the condition of the *Porphyra angusta* growth was changed to: temperature: 20° C., illuminance: 2000 lx and light/dark ratio: 14:10. After cultivating for 40 days, the weight of dried *Porphyra angusta* is 28.8 times the weight of the inoculated filaments.

EXAMPLE 15

The procedures as described in example 11 were repeated, except that the condition of the *Porphyra angusta* growth was changed to: temperature: 15° C., illuminance: 2000 lx and light/dark ratio: 12:12 . After cultivating for 40 days, the weight of dried *Porphyra angusta* is 20.1 times the weight of the inoculated filaments.

EXAMPLE 16

The procedures as described in example 11 were repeated, except that the condition of the *Porphyra angusta* growth was changed to: temperature: 25° C., illuminance: 2000 lx and light/dark ratio: 12:12. After cultivating for 40 days, the weight of dried *Porphyra angusta* is 17.1 times the weight of the inoculated filaments.

EXAMPLE 17

The procedures as described in example 11 were repeated, except that the condition of the *Porphyra angusta* growth was changed to: temperature: 25° C., illuminance: 4000 lx and light/dark ratio: 14:10. After cultivating for 40 days, the weight of dried *Porphyra angusta* is 20.3 times the weight of the inoculated filaments.

EXAMPLE 18

The procedures as described in example 11 were repeated, except that the condition of the *Porphyra angusta* growth was changed to: temperature: 30° C., illuminance: 1000 lx and light/dark ratio: 12:12. After cultivating for 40 days, the weight of dried *Porphyra angusta* is 14.0 times the weight of the inoculated filaments.

EXAMPLE 19

The procedures as described in example 11 were repeated, except that *Porphyra angusta* instead of *Bangia atropurpurea* as cultivated material was used, and the condition of the *Porphyra angusta* growth was changed to: temperature: 30° C., illuminance: 1000 lx and light/dark ratio: 10:14. After cultivating for 40 days, the weight of dried *Porphyra angusta* is 14.1 times the weight of the branched original filaments.

EXAMPLE 20

The procedures as described in example 11 were repeated, except that the condition of the *Porphyra angusta* growth was changed to: temperature: 30° C., illuminance: 1000 lx and light/dark ratio: 16:8. After cultivating for 40 days, the weight of dried *Porphyra angusta* is 13.3 times the weight of the inoculated filaments.

EXAMPLE 21

The procedures as described in example 10 were repeated, except that *Porphyra angusta* instead of *Bangia atropurpurea* as raw material was used. Phycoerythrin solution in the tubes from #45 to #59 was collected. The $OD_{565}/OD_{280}$ of the obtained phycoerythrin is 5.2 and the purity is 99% after analyzing with SDS-PAGE.

It is evident to show that the invented process has the following advantages:

1. Unlike previously developed methods of phycoerythrin extraction from Porphyra or Ceramium thallus, the process does not require heating or gel eliminating procedures. It just needs drying, grinding, dissolving and then gel filtration separating.

2. The collection of cultivated filaments can be conveniently acquired by a net; unlike the collection method of the single-cell alga Porphyridium, which may secret gel-polysaccharides, causing difficulties in collection and purification.

3. The culture medium after the harvest of *Bangia atropurpurea* or *Porphyra angusta* can be recovered for further inoculation, reducing the waste that other algae culture methods may produce.

4. The gel-like phycoerythrin obtained from salting-out process is a stabilized form, and can therefore be preserved directly or freeze-dried after dialyzing.

5. Cultivated *Bangia atropurpurea* or *Porphyra angusta* as raw material for phycoerythrin production can give a more confirm, reliable and stable product due to the consistency of culture condition.

6. A mixture of phycocyanin and allophycocyanin can be obtained through gel filtration for the purification of phycoerythrin. The mixture can then be separated into pure phycocyanin and allophycocyanin by DEAE-Sephacel ion exchange chromatography and NaCl gradient elution.

What is claimed is:

1. A process for preparing crude gel-form phycoerythrin concentrate from red algae, comprising the following steps:
    a) providing a mature red algae thalli selected from the group consisting of *Bangia atropurpurea* gametophytes and *Porphyra angusta* gametophytes;
    b) cultivating said red algae thalli in a SWM-III medium to obtain spores therefrom;
    c) cultivating said spores in a condition wherein the temperature, light intensity and daily illuminating period are respectively 15° C.–25° C., 1000 lx–4000 lx and 10–16 hours to germinate filaments;

d) breaking up said filaments into minute segments and cultivating them in a larger tank in the above condition until the cultivated filaments grow to the required amounts;
e) collecting said cultivated filaments, drying and grinding them into powder;
f) adding said powder to a liquid selected from the group consisting of water and phosphate solution to obtain a clear-red pigment protein solution containing said phycoerythrin; and
g) salting out said gel-form phycoerythrin concentrate from said clear-red pigment protein solution.

2. The process as claimed in claim 1, further comprising the step of dialyzing said gel-form phycoerythrin concentrate and purifying the phycoerythrin by gel filtration therefrom.

3. The process as claimed in claim 1, wherein said SWM-III medium is an inorganic SWM-III medium.

4. The process as claimed in claim 1, wherein the cultivating condition of step c) is: temperature: 20° C, light intensity: 2000 lx and daily illuminating period: 12 hours.

5. The process as claimed in claim 1, wherein in step e) the drying of *Bangia atropurpurea* filaments is conducted in vacuum.

6. The process as claimed in claim 1, wherein in step e) the drying of *Bangia atropurpurea* filaments method is conducted by using warm air.

7. The process as claimed in claim 1, wherein in step e) the cultivated red algae filaments is collected by using a net of 200 mesh.

8. The process as claimed in claim 1, wherein in step g) the phycoerythrin is salted out by using 20%–30% $(NH_4)_2SO_4$ and 60%–65% $(NH_4)_2SO_4$.

9. The method as claimed in claim 2, wherein the gel filtration is a Sephadex G200 gel filtration.

* * * * *